(12) United States Patent
Inoue

(10) Patent No.: US 11,568,158 B2
(45) Date of Patent: Jan. 31, 2023

(54) INFORMATION PROCESSING APPARATUS AND INFORMATION PROCESSING METHOD

(71) Applicant: TOSHIBA TEC KABUSHIKI KAISHA, Tokyo (JP)

(72) Inventor: Akiko Inoue, Tagata Shizuoka (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/323,998

(22) Filed: May 18, 2021

(65) Prior Publication Data
US 2022/0083751 A1 Mar. 17, 2022

(30) Foreign Application Priority Data
Sep. 14, 2020 (JP) .............................. JP2020-153874

(51) Int. Cl.
*G06K 7/10* (2006.01)
*G16H 70/40* (2018.01)
(52) U.S. Cl.
CPC ......... *G06K 7/10366* (2013.01); *G16H 70/40* (2018.01)

(58) Field of Classification Search
CPC .......................... G06K 7/10366; G16H 70/40
See application file for complete search history.

(56) References Cited

U.S. PATENT DOCUMENTS
2013/0311311 A1* 11/2013 Chopra .................. G06Q 50/12 705/15

FOREIGN PATENT DOCUMENTS
JP 2005-63338 A 3/2005

* cited by examiner

*Primary Examiner* — Jamara A Franklin
(74) *Attorney, Agent, or Firm* — Kim & Stewart LLP

(57) ABSTRACT

According to an embodiment, an information processing apparatus acquires, on the basis of tag information read by a wireless tag read from a wireless tag attached to a product, allergen information indicating an allergen contained in the product. Further, the information processing apparatus accepts an input of designation information for designating a product whose allergen information is to be output. Further, the information processing apparatus outputs the acquired allergen information for a product designated on the basis of he accepted designation information.

10 Claims, 10 Drawing Sheets

INFORMATION PROCESSING APPARATUS AND INFORMATION PROCESSING METHOD

CROSS-REFERENCE TO RELATED APPLICATIONS

This application is based upon and claims the benefit of priority from the prior Japanese Patent Application No. 2020-153874, filed on Sep. 14, 2020, the entire contents of which are incorporated herein by reference.

FIELD

An embodiment to be described here generally relates to an information processing apparatus and an information processing method.

BACKGROUND

In recent years, adverse health effects caused by food allergy have become a problem. Under such a background, in supermarkets and the like, information regarding an allergen that is a causative material of food allergy is provided to customers who purchase food products. As a result, the customer can know the allergen contained in the product to be purchased and can refrain from purchasing the product containing the allergen that adversely affects the customer or the family.

As an example of an apparatus that provides such information regarding an allergen, a system in which information regarding an allergen contained in a product is stored in an RFID tag (hereinafter, referred to also as a wireless tag) and the information stored in the wireless tag (hereinafter, referred to also as tag information) is read by a wireless tag reader is known. In this system, the wireless tag reader reads the tag information of the wireless tag attached to a product display shelf to read allergen information of all the products displayed on the product display shelf. Then, the above-mentioned system displays the corresponding product and allergen when the wireless tag reader reads the allergen information registered in advance by a customer.

In the existing technology described above, the allergen information read by the wireless tag reader is narrowed down in accordance with the type of allergen and provided to the customer. However, in the existing technology, since the allergen information read by the wireless tag reader is not narrowed down in accordance with the product, the allergen information is displayed even for the product that the customer does not intend to purchase. For this reason, many pieces of allergen information not required by the customer are displayed, which may make it difficult to grasp the allergen information.

DETAILED DESCRIPTION

Figure 1:
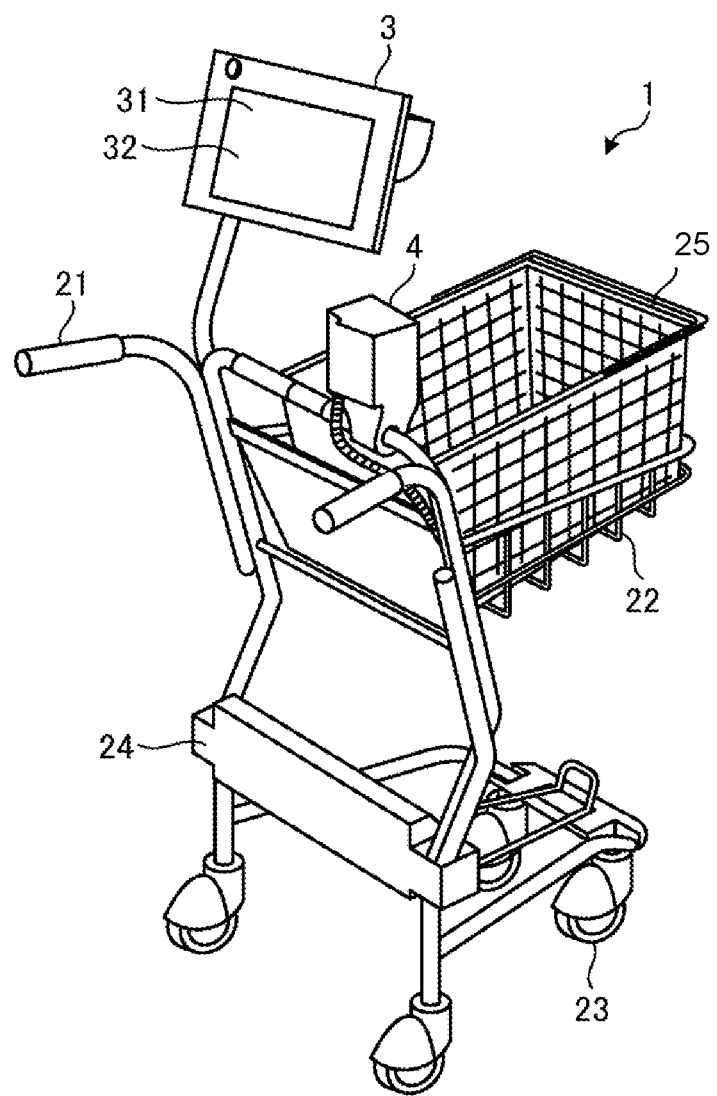
FIG. 1 is a perspective view showing an external appearance of a shopping cart including an information processing apparatus according to an embodiment.

According to an embodiment, an information processing apparatus includes a wireless tag reader, a storage device, and a processor. The wireless tag reader reads, from a wireless tag attached to a product, tag information stored in the wireless tag. The tag information includes identification data of the product to which the wireless tag is attached. The storage device holds a product master file for storing, in association with the identification data, allergen information indicating an allergen contained in the product specified by the identification data. The processor acquires, from the product master file, the allergen information of the product specified by the identification data included in the tag information read by the wireless tag reader. The processor accepts an input of designation information for designating one of products specified by the identification data included in the tag information read by the wireless tag reader. Further, the processor outputs allergen information of a product designated on the basis of the accepted designation information, of the acquired allergen information.

Hereinafter, an information processing apparatus according to the embodiment will be described with reference to the drawings. The same reference symbols in the drawings denote the same or similar portions. In this embodiment, the information processing apparatus is described as a registration apparatus provided in a shopping cart (hereinafter, referred to also simply as a cart), but the information processing apparatus according to this embodiment is not limited thereto.

FIG. 1 shows a diagram showing an external appearance of a cart 1 including an information processing apparatus. The cart 1 is used in a store such as a supermarket. The cart 1 includes a cart main body 2, a registration apparatus 3, and a wireless tag reader 4.

The cart main body 2 is an apparatus that houses a product to be purchased by a customer directly or via a basket 25 while moving in a store by being operated by the customer. The cart main body 2 includes a handle 21, a basket placing portion 22, a caster 23, a battery holder 24, and the like. The cart main body 2 is an example of a container that moves together with a customer and houses a product to be purchased by the customer.

A pair of the handles 21 is provided to project to the side of the cart main body 2 where the customer is located, i.e., to the side opposite to the basket placing portion 22. The handle 21 is for the customer to grasp and move the cart main body 2. The basket placing portion 22 is a table on which the basket 25 for housing a product to be purchased by the customer is placed.

Four casters 23 are provided in the cart main body 2. Each caster 23 can be rotated individually, so that the cart main body 2 can be pushed by the customer to move freely in the store. The battery holder 24 attachably/detachably holds a battery (not shown). The battery supplies electric power to the wireless tag reader 4.

The registration apparatus 3 is, for example, a tablet terminal, and is attachably/detachably attached to the cart main body 2. The registration apparatus 3 includes a display 31 and a touch panel 32 as an input device. The registration apparatus 3 registers sales of products purchased by customers (hereinafter, referred to as "product registration") and displays information regarding allergens contained in products displayed in the store, and is an example of the information processing apparatus. Note that the sales registration includes processing of storing product information (product name, price, etc.) of the product on the basis of the acquired product code (product identification data). Further, the registration apparatus 3 may be provided in the basket 25. In this case, the basket 25 is an example of a container that moves together with a customer and houses a product to be purchased by the customer, and the customer can use the registration apparatus 3 while shopping without using the cart 1.

The display 31 includes, for example, a liquid crystal panel, and displays various types of information. The display 31 functions also as an output device for outputting information output by a controller 300 (see FIG. 3) of the registration apparatus 3. Note that the output device for outputting information output by the controller 300 may be provided separately from the registration apparatus 3. Further, the output device may be any device as long as the output device notifies the customer of information, is not limited to a device that outputs information on a display screen, and may output information by voice, for example. The touch panel 32 is an input device that is provided on the surface of the display 31 and inputs information corresponding to the touched position to the controller 300 of the registration apparatus 3, and functions as an operation input unit for inputting an operation of the user. Note that the details of the registration apparatus 3 will be described below.

Figure 7:
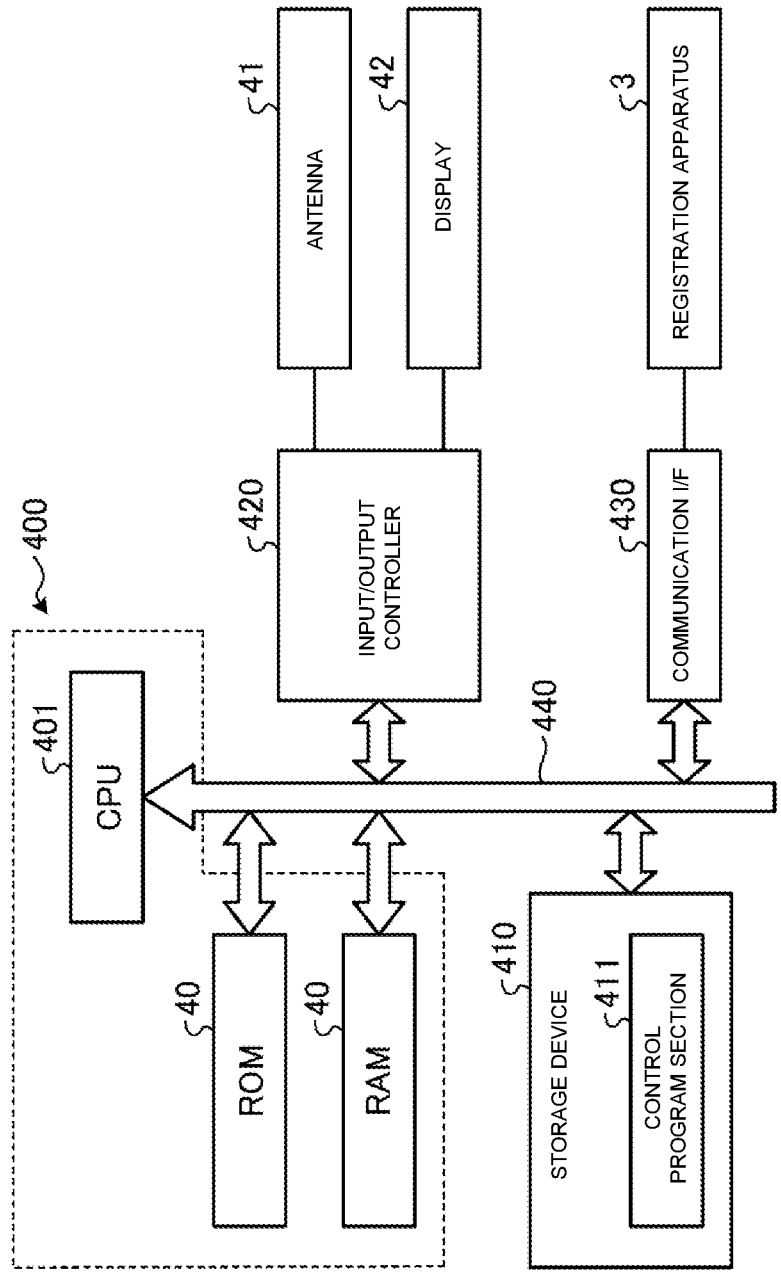
FIG. 7 is a block diagram showing a hardware configuration of a wireless tag reader according to the embodiment.
Figure 8:
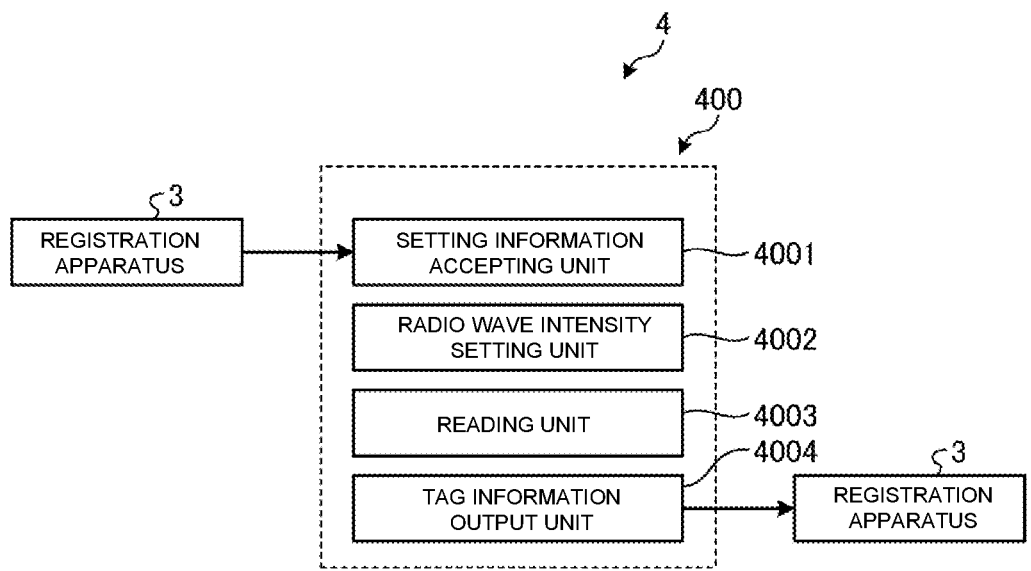
FIG. 8 is a block diagram showing a functional configuration of the wireless tag reader according to the embodiment.

The wireless tag reader 4 reads tag information from a wireless tag attached to the product housed in the basket 25 or from a wireless tag 43 (see FIG. 2) attached to the product displayed on the product display shelf by varying the radio wave strength of the radio wave transmitted from an antenna 41 (see FIG. 7). The tag information of the wireless tag 43 attached to the product includes a product code for specifying the product and an individual-item code for specifying the individual item of the product. Note that since the wireless tag attached to the product housed in the basket 25 and the wireless tag 43 attached to the product displayed on the product display shelf are wireless tags having the same configuration, the wireless tag attached to the product housed in the basket 25 is also referred to as the wireless tag 43 using the same reference symbol in the following description. Further, details of the wireless tag reader 4 will be described below.

Figure 2:
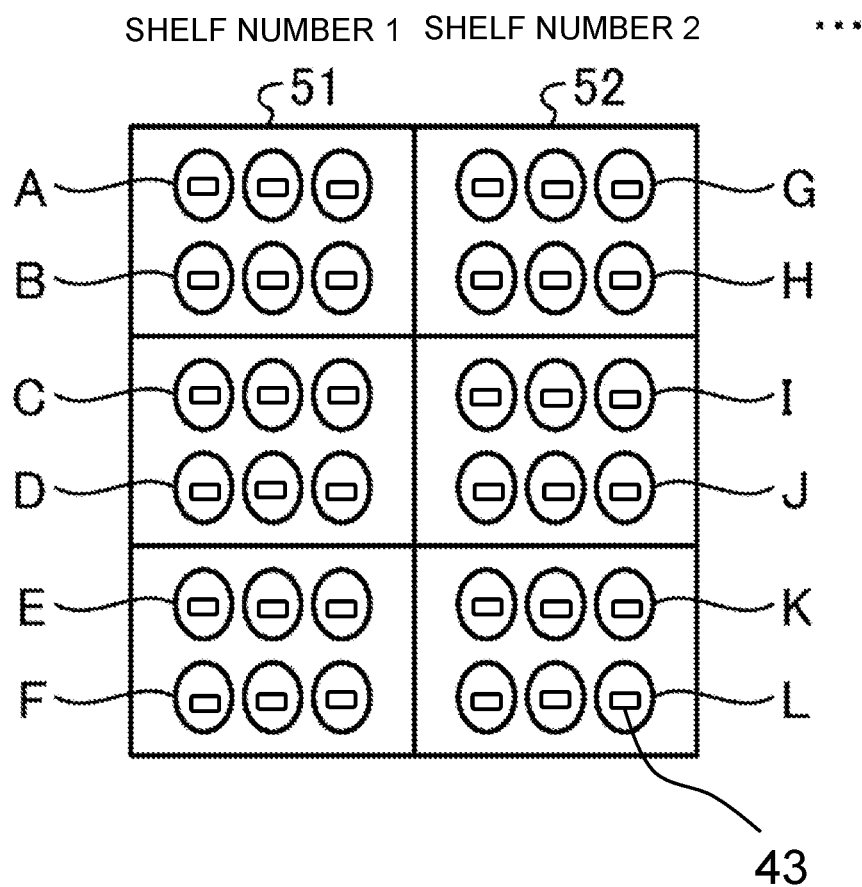
FIG. 2 is a diagram schematically showing a product display shelf of a store to which the shopping cart according to the embodiment is applied.

FIG. 2 is a diagram schematically showing a product display shelf of a store in which the cart 1 is used. A plurality of product display shelves 51, 52, . . . having shelf numbers are provided in the store. Products are displayed on each of the product display shelves. For example, a plurality of products A to a plurality of products F classified for each product code are displayed on the product display shelf 51. Similarly, a plurality of products G to a plurality of products L are displayed on the product display shelf 52. The wireless tag 43 is attached to each of the products, i.e., each individual item. As described above, the wireless tag 43 stores, as tag information, a product code for specifying a product, an individual item code for specifying an individual item, and the like. The tag information of the wireless tag 43 is read by the wireless tag reader 4 provided in the cart main body 2 that moves together with the customer.

Figure 3:
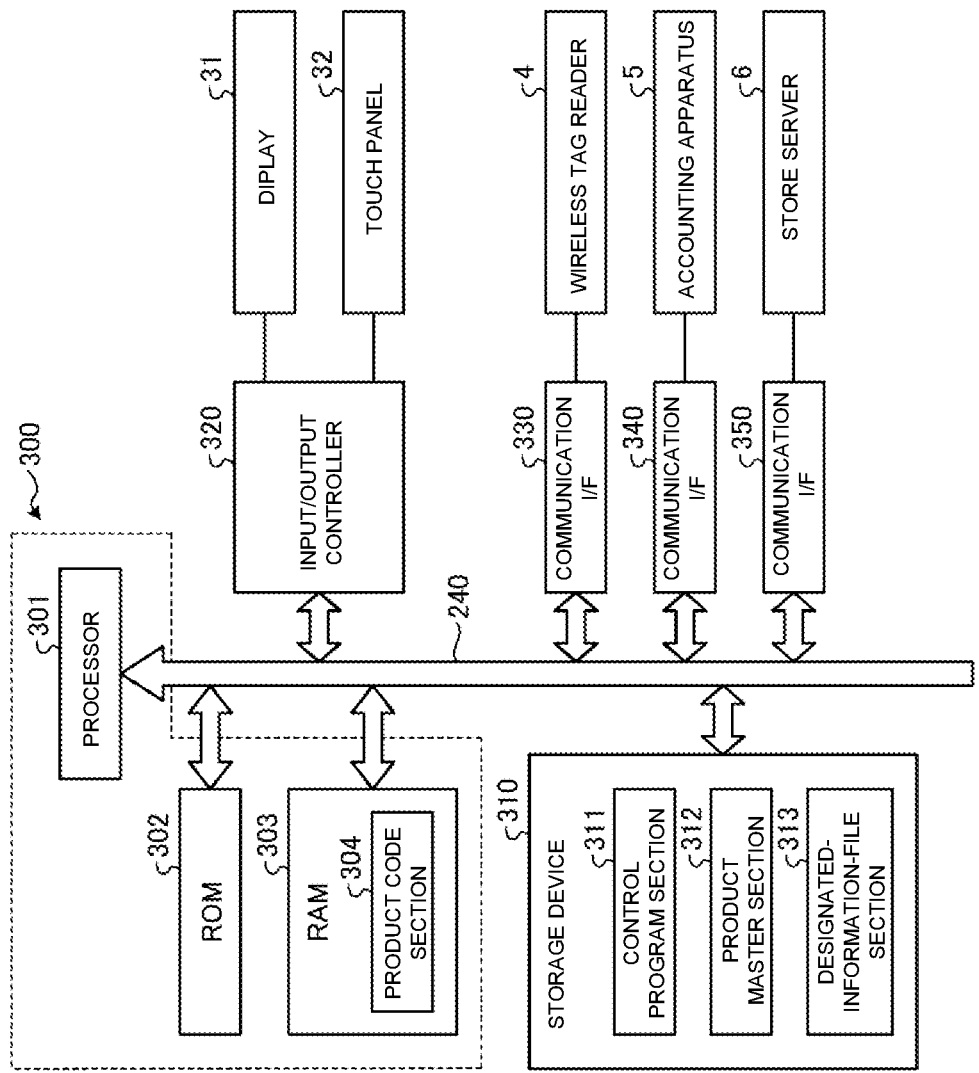
FIG. 3 is a block diagram showing a hardware configuration of the information processing apparatus according to the embodiment.

Next, the registration apparatus 3 will be described in detail. FIG. 3 is a block diagram showing a hardware configuration of the registration apparatus 3. The registration apparatus 3 includes the controller 300, a storage device 310, an input/output controller 320, and communication I/Fs (Interfaces) 330 to 350. The controller 300, the storage devices 310, the input/output controller 320, and the communication I/Fs 330 to 350 are connected to each other via a bus 360.

The controller 300 includes a computer including a processor 301, and memories 302 and 303. The processor 301 is, for example, a central processing unit (CPU). The memories 302 and 303 are, for example, a ROM (Read Only Memory) 302 and a RAM (Random Access Memory) 303, respectively. The processor 301, the ROM 302, and the RAM 303 are connected to each other via the bus 360.

The processor 301 controls the operation of the entire registration apparatus 3. The ROM 302 stores various programs such as programs used to drive the CPU 301 and various types of data. The RAM 303 includes a product code section 304. The product code section 304 is an area for storing a product code received from the wireless tag reader 4. Further, the RAM 303 is used as a work area of the CPU 301 and expands various programs and various types of data stored in the ROM 302 and the storage device 310. The controller 300 executes various types of control processing of the registration apparatus 3 by the processor 301 operating in accordance with the control program that is stored in the ROM 302 or the storage device 310 and expanded to the RAM 303.

The storage device 310 includes a control program section 311, a product master section 312, and a designated-information-file section 313. The storage devices 310 includes a rewritable non-volatile storage medium such as an HDD (Hard Disk Drive), an SSD (Solid State Memory), and a flush memory. The storage device 310 includes a control program section 311, a product master section 312, and a designated-information-file section 313. The control program section 311 is an area for storing various control programs in addition to the control program for functioning as the registration apparatus 3.

Figure 4:
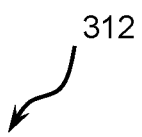
FIG. 4 is a diagram showing a data configuration of a product master section according to the embodiment.

The product master section 312 is an area for storing a product master. FIG. 4 is a diagram showing a data configuration of the product master section 312. The product master is a master file in which product codes, product names, prices, and pieces of allergen information (hereinafter, collectively referred to as product information) are stored in association with each other for products handled in a store. The product code indicates the code set to specify the product. The product name indicates the name of the product, and the price indicates the unit price of the product.

The allergen information indicates an allergen contained in the product. The allergen is a causative material of food allergy contained in the product, and indicates a "specific raw material" for which display specified by Cabinet Order or the like is mandatory, and "those equivalent to specific raw materials" for which display is recommended. In this embodiment, seven items of specific raw materials such as eggs and wheat and 20 items of those equivalent to specific raw materials such as soybeans and Japanese yams are set as allergens. The setting of allergens can be performed as appropriate in accordance with the revision of Cabinet Order or the like. Note that since products handled in the store change from day to day, the product master is appropriately updated by a store server 6 connected via the communication I/F 350.

Figure 5:
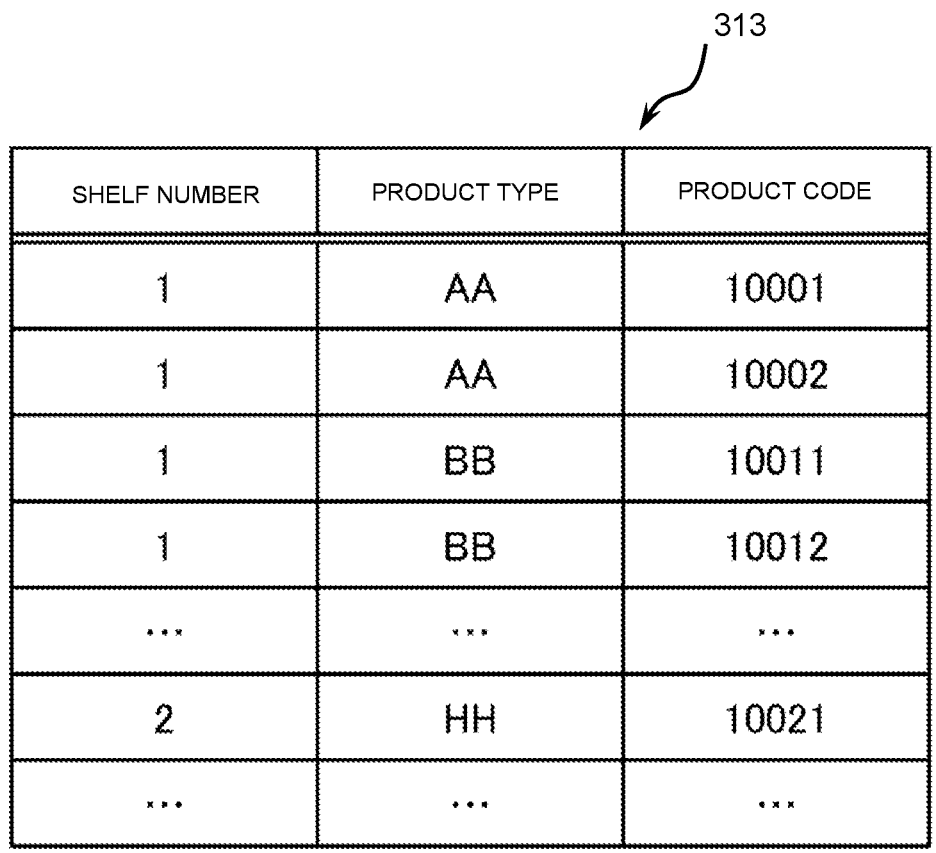
FIG. 5 is a diagram showing a data configuration of a designated-information-file section according to the embodiment.

The designated-information-file section 313 is an area for storing a designation information file. FIG. 5 is a diagram showing a data configuration of the designated-information-file section 313. The designation information file is used when a customer designates a product of which allergen information is displayed, of products whose tag information has been read by the wireless tag reader 4. The designation information file stores shelf numbers, product types, and product codes in association with each other.

The shelf number indicates a number set to specify a product display shelf installed in the store. The product type indicates, for example, the type of product such as "biscuit" and "cookie". Product codes of a plurality of products having different product names are stored in association with one product type. The product code indicates a code for specifying a product as described above. Note that since the arrangement of the products in the store changes daily, the designation information file is also updated accordingly by the store server 6 connected via the communication I/F 350.

Now, description is made with reference to FIG. 3 again. The input/output controller 320 is connected to the display 31 and the touch panel 32. The input/output controller 320 has a function as an input/output interface to the connected hardware and a function for controlling the hardware. As a result, the controller 300 is capable of transmitting/receiving information (data) to/from the display 31 and the touch panel 32 via the input/output controller 320. The display 31 and the touch panel 32 can be controlled on the basis of an instruction of the controller 300.

The communication I/F 330 is an interface for communicating with the wireless tag reader 4. The communication I/F 340 is an interface for communicating with an accounting apparatus 5 when, for example, paying for the product for which product registration has been performed by the registration apparatus 3. The communication I/F 350 is an interface for communicating with the store server 6 when, for example, updating the product master and the designation information file. The controller 300 is capable of transmitting and receiving, by being connected to the wireless tag reader 4, the account apparatus 5, and the store server 6 via the communication I/Fs 330 to 350, information (data) to/from these apparatuses.

Figure 6:
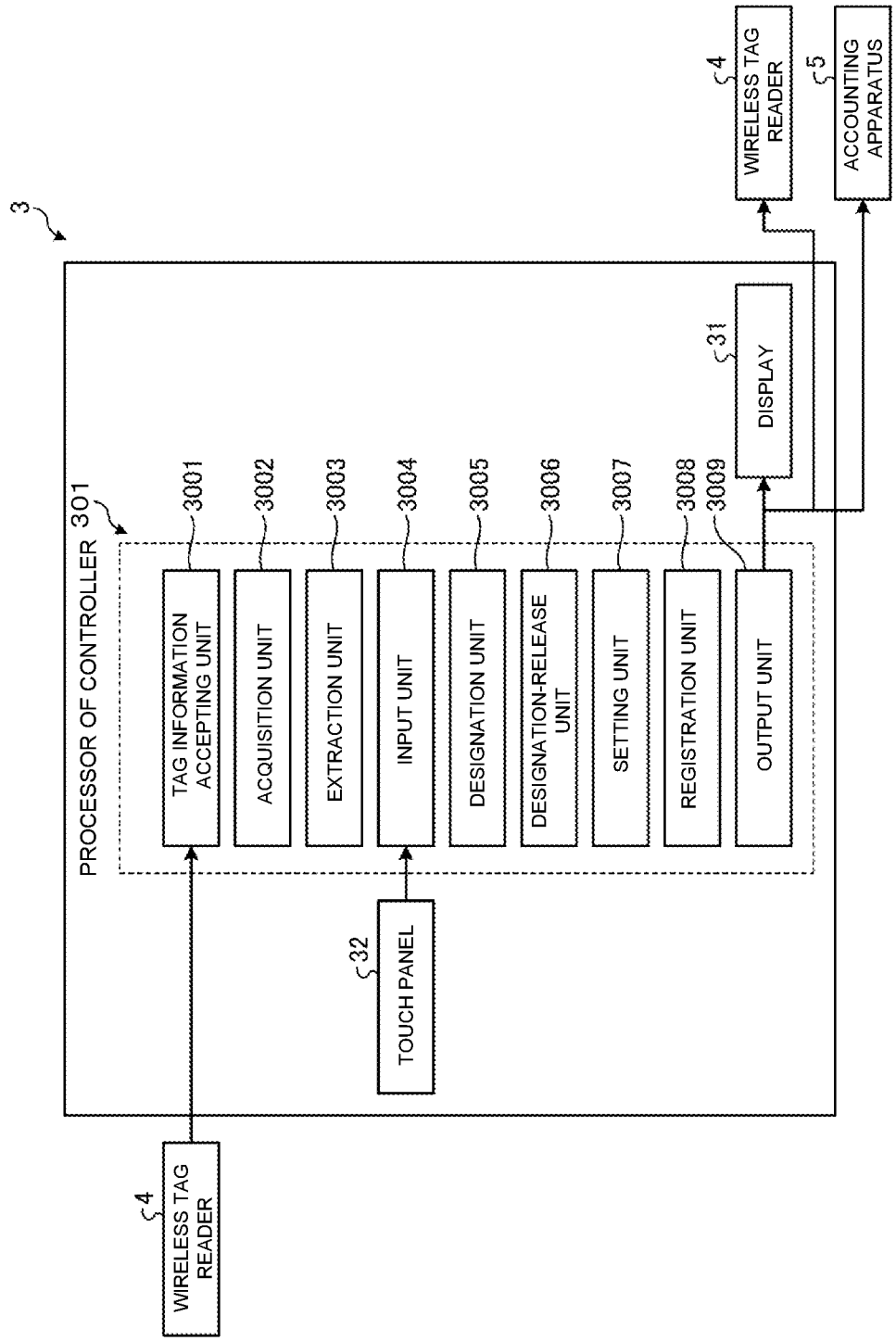
FIG. 6 is a block diagram showing a functional configuration of the information processing apparatus according to the embodiment.

Next, a functional configuration of the processor 301 of the controller 300 of the registration apparatus 3 will be described. FIG. 6 is a block diagram showing a functional configuration of the controller 300 of the registration apparatus 3. The processor 301 of the controller 300 operates in accordance with a control program stored in the ROM 302 or the storage device 310, thereby functioning as a tag information accepting unit 3001, an acquisition unit 3002, an extraction unit 3003, an input unit 3004, a designation unit 3005, a designation-release unit 3006, a setting unit 3007, a registration unit 3008, and an output unit 3009. Note that the above-mentioned functional configurations may be implemented in hardware.

The tag information accepting unit 3001 receives, from the wireless tag reader 4, the tag information read by the wireless tag reader 4 and accepts the received tag information. The tag information accepting unit 3001 accepts the tag information from the wireless tag reader 4 at timings of predetermined intervals or at timings designated by the customer. The tag information accepted by the tag information accepting unit 3001 includes a product code and an individual item code. For this reason, in the following description, accepting the tag information by the tag information accepting unit 3001 will be referred to as accepting the product code or accepting the individual item code in some cases.

The acquisition unit 3002 acquires allergen information indicating an allergen contained in the product on the basis of the tag information read by the wireless tag reader 4, of the wireless tags 43 (see FIG. 2) attached to the plurality of products. Specifically, the acquisition unit 3002 reads and acquires, from the product master section 312 (see FIG. 4), the product information including the allergen information corresponding to the product code accepted by the tag information accepting unit 3001. Note that all the pieces of product information may be stored in the wireless tag 43 attached to the product. In this case, the acquisition unit 3002 acquires the product information from the tag information accepting unit 3001 without reading the product information from the product master section 312.

The extraction unit 3003 refers to the designated-information-file section 313 shown in FIG. 5, and selects, of the product type (e.g., 'AA' and 'BB' in FIG. 5) corresponding to the product code (e.g., '10001' and '10011') accepted by the tag information accepting unit 3001, the product type (e.g., 'AA' in FIG. 5) corresponding to the largest number of product codes. Then, the extraction unit 3003 extracts product codes ('10001' and '10002' in FIG. 5) of the product that belongs to the selected product type. Normally, in a store, products are placed on product display shelves for each product type (see FIG. 2). The extraction unit 3003 specifies the type of a product placed on a product display shelf to which the customer approaches, estimates the products that belong to this product type as the products of the customer's interest, and extracts the product codes of these products. In other words, the extraction unit 3003 calculates, on the basis of the type of the product specified by the product code included in the tag information accepted by the tag information accepting unit 3001, the number of the product codes for each type read by the wireless tag reader, and extracts the product code of the product to be output in accordance with the calculated number of the product codes for each type.

The input unit 3004 accepts an input of designation information for designating a product whose allergen information is to be output. Specifically, the input unit 3004 inputs, as the designation information, the product code extracted by the extraction unit 3003. Further, the input unit 3004 inputs, as the designation information, the product code of the product specified on the basis of the information input to the touch panel 32 by the customer. Since the registration apparatus 3 according to this embodiment includes the designated-information-file section 313 shown in FIG. 5 in which the shelf number, the product type, and the product code are stored in association with each other, the customer can specify a plurality of products in one operation by inputting the shelf number or the product type to the touch panel 32. Further, the designation-release information and the setting information input to the touch panel 32 are input to the input unit 3004. The designation-release information is information for instructing to release the designation of the product by the designation unit 3005, which will be described below. The setting information is information for instructing to set the radio wave intensity of the wireless tag reader 4 by the setting unit 3007 described below to be weak.

The designation unit 3005 designates a product on the basis of the designation information input to the input unit 3004. Specifically, the designation unit 3005 temporarily stores, in the RAM 303, the product code of the product specified by the product code input to the input unit 3004 from the extraction unit 3003 or the product code input to the input unit 3004 on the basis of the information from the touch panel 32, as the product that is an allergen-display target. That is, the product code input to the input unit 3004 is an example of the designation information.

The designation-release unit 3006 releases the designation of the product by the designation unit 3005. Specifically, the designation-release unit 3006 temporarily stops the function of the designation unit 3005 on the basis of the designation-release information input from the touch panel 32 to the input unit 3004. By operating the touch panel 32 to release the designation of the product by the designation unit 3005, the customer can check all pieces of allergen information acquired by the acquisition unit 3002, i.e., the allergen information of all the products whose tag information has been read by the wireless tag reader 4.

The setting unit 3007 performs processing for setting the reading range of the wireless tag reader 4. The reading range of the wireless tag reader 4 in this embodiment can be set to a first reading range in which tag information is read from the wireless tag 43 (see FIG. 2) attached to a product displayed in a product display shelf of the store, and to a second reading range in which tag information of the wireless tag 43 attached to a product housed in a container is read, which is narrower than the first reading range. The setting unit 3007 instructs the radio wave strength of the radio wave transmitted by the antenna 41 of the wireless tag reader 4 to the wireless tag reader 4 via the output unit 3009 on the basis of the setting information input from the touch panel 32 to the input unit 3004.

The registration unit 3008 registers sales of the product purchased by the customer on the basis of the product code included in the tag information read by the wireless tag reader 4 while the second reading area is set by the setting unit 3007. Specifically, in the case where the reading range of the wireless tag reader 4 is in a state where the tag information of the wireless tag 43 located in the basket 25 is read, the registration unit 3008 executes the product registration on the basis of the product code acquired by the acquisition unit 3002. The product registration is performed by the registration unit 3008 referring to the product master section 312 and storing, in the RAM 303, the product information corresponding to the product code acquired by the acquisition unit 3002.

The output unit 3009 outputs the allergen information acquired by the acquisition unit 3002 for the product designated by the designation unit 3005. Specifically, the output unit 3009 outputs, to the display 31, the allergen information acquired by the acquisition unit 3002 for the product designated by the designation unit 3005. Further, the output unit 3009 outputs first information indicating that the reading range of the wireless tag reader 4 is set to the first reading range and second information indicating that the reading range is set to the second reading range in accordance with the setting of the setting unit 3007. Further, when the customer makes a payment, the output unit 3009 outputs, to the accounting apparatus 5, the registration information of the product registered by the registration unit 3008, i.e., the product information stored in the RAM 303.

Next, the wireless tag reader 4 will be described in detail. FIG. 7 is a block diagram showing a hardware configuration of the wireless tag reader 4. The wireless tag reader 4 includes a controller 400, a storage device 410, an input/output controller 420, a communication I/F (Interface) 430, and the like. The controller 400, the storage device 410, the input/output controller 420, and the communication I/F 430 are connected to each other via a bus 440.

The controller 400 includes a computer including a processor 401 and memories 402 and 403. The processor 401 is, for example, a CPU. The memories 402 and 403 are, for example, a ROM 402 and a RAM 403, respectively. The processor 401, the ROM 402, and the RAM 403 are connected to each other via the bus 440.

The processor 401 controls the operation of the entire wireless tag reader 4. The ROM 402 stores various programs such as programs used to drive the processor 401 and various types of data. The RAM 403 is used as a work area of the processor 401 and expands various programs and various types of data stored in the ROM 402 or the storage device 410. The processor 401 of the controller 400 operates in accordance with the control program that is stored in the ROM 402 or the storage device 410 and expanded to the RAM 403, thereby executing various types of control processing of the wireless tag reader 4.

The storage device 410 includes, for example, a rewritable non-volatile storage medium such as an HDD (Hard Disk Drive), an SSD (Solid State Memory), and a flush memory. The storage device 410 includes a control program section 411. The control program section 411 is an area for storing various control programs in addition to the control program for functioning as the wireless tag reader 4.

The input/output controller 420 is connected to the antenna 41 and the display 42. The antenna 41 transmits a carrier wave (radio wave) in accordance with the instruction of the controller 400, and receives a response wave (radio wave) transmitted by the wireless tagging 43 in response to the carrier wave. A plurality of antennas 41 may be provided. The display 42 displays various types of information. The input/output controller 420 has a function as an input/output interface to the connected hardware and a function for controlling the hardware. As a result, the controller 400 is capable of transmitting/receiving information (data) to/from the antenna 41 and the display 42 via the input/output controller 420. Further, the antenna 41 and display 42 can be controlled on the basis of the instruction of the controller 400.

The communication I/F 430 is an interface for communicating with the registration apparatus 3. As a result, the controller 400 is capable of transmitting/receiving information (data) to/from the registration apparatus 3 via the communication I/F 430.

Next, a functional configuration of the processor of the controller 400 of the wireless tag reader 4 will be described. FIG. 6 is a block diagram showing a functional configuration of the controller 400 of the wireless tag reader 4. The processor 401 of the controller 400 operates in accordance with a control program stored in the ROM 402 or the storage device 410, thereby functioning as a setting information accepting unit 4001, a radio wave intensity setting unit 4002, a reading unit 4003, and a tag information output unit 4004. Note that the above-mentioned functional configurations may be implemented in hardware.

The setting information accepting unit 4001 accepts, from the registration apparatus 3, setting information indicating the reading area set by the setting unit 3007 of the registration apparatus 3. That is, the setting information accepting unit 4001 accepts the first information indicating that the reading range of the wireless tag reader is set to the first reading range and the second information indicating that the reading range is set to the second reading range. For example, the setting information accepting unit 4001 is capable of accepting the second information by accepting information indicating the start of the product registration from the registration apparatus 3. Further, the setting information accepting unit 4001 is capable of accepting the first information by accepting information indicating the end of the product registration from the registration apparatus 3.

The radio wave intensity setting unit 4002 sets, on the basis of the setting information accepted by the setting information accepting unit 4001, the strength of the radio wave transmitted by the antenna 41. The radio wave intensity setting unit 4002 sets, when the setting information accepting unit 4001 accepts the first information, the intensity of the radio wave transmitted by the antenna 41 to first radio wave intensity. Further, the radio wave intensity setting unit 4002 sets, when the setting information accepting unit 4001 accepts the second information, the intensity of the radio wave transmitted by the antenna 41 to second radio wave intensity lower than the first radio wave intensity.

The reading unit 4003 reads the tag information of the wireless tag 43 on the basis of the response wave from the wireless tag 43 received by the antenna 41. More specifically, the reading unit 4003 reads the product code, the individual item code, and the like included in the tag information. In the case where the radio wave intensity is set to the first radio wave intensity, the reading unit 4003 is capable of reading the tag information of the wireless tag 43 attached to the product displayed on the product display shelf. Further, in the case where the radio wave intensity is set to the second radio wave intensity, the reading unit 4003 does not read the tag information of the wireless tag 43 attached to the product displayed on the product display shelf, but reads the tag information of the wireless tag 43 attached to the product housed in the cart main body 2 such as the basket 25.

The tag information output unit 4004 outputs the tag information read by the reading unit 4003 to the registration apparatus 3.

Figure 9:
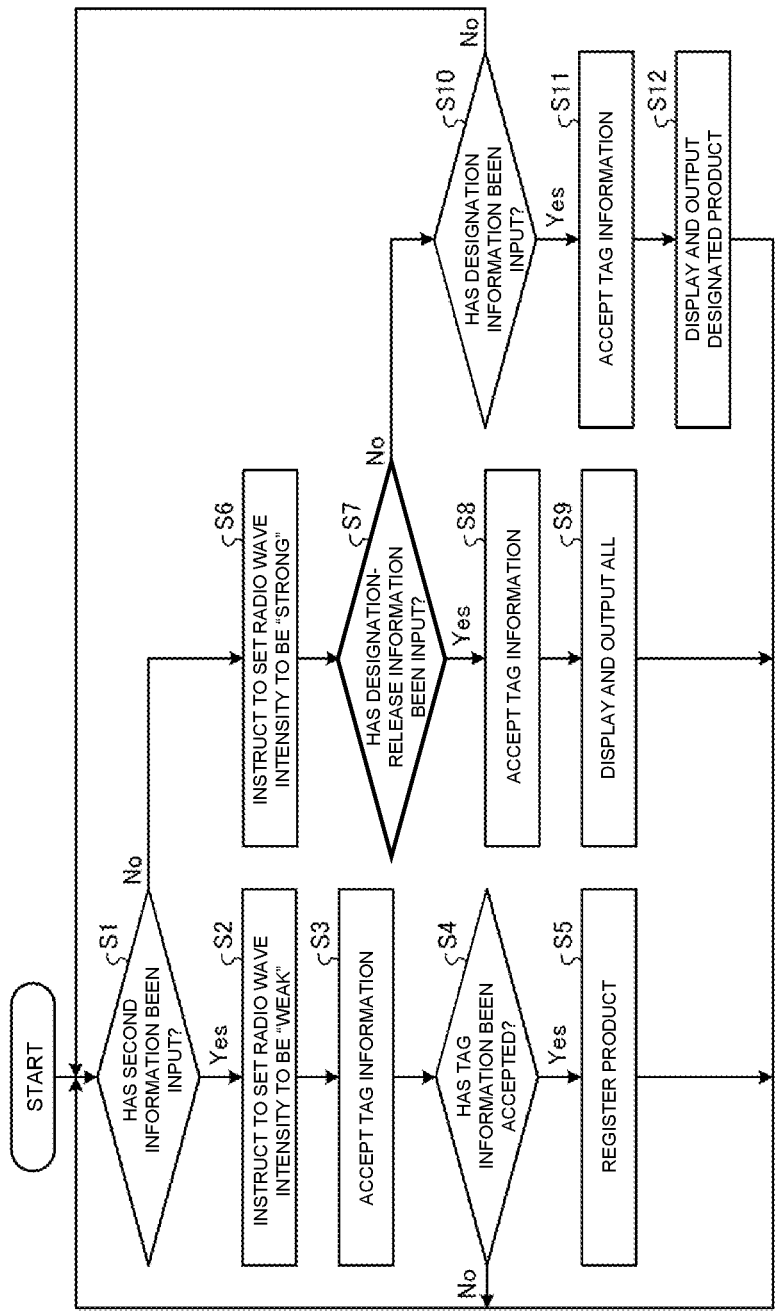
FIG. 9 is a flowchart showing processing of a controller of the information processing apparatus according to the embodiment.

The processing executed by the registration apparatus 3 when a customer shops using the cart 1 on the basis of the above-mentioned configuration will be described. FIG. 9 is a flowchart showing the processing of the processor 301 of the controller 300 of the registration apparatus 3.

First, in Step S1, the input unit 3004 of the processor 301 determines whether or not second information has been input as setting information. For example, the input unit 3004 of the processor 301 determines whether or not the customer has touched a product registration button of the touch panel 32 in order to perform the product registration of the product housed in the basket 25. In the case where it is determined that the second information has been input (Yes in Step S1), the processing of the processor 301 proceeds to Step S2. In Step S2, the setting unit 3007 of the processor 301 sets the radio wave intensity to be weak. The output unit 3009 of the processor 301 outputs second information for instructing the wireless tag reader 4 to set the radio wave intensity to be weak.

Then, in Step S3, the tag information accepting unit 3001 of the processor 301 starts accepting the tag information. In Step S4, whether or not the tag information accepting unit 3001 of the processor 301 has accepted the tag information from the wireless tag reader 4. In the case where it is determined that the tag information has been accepted (Yes in Step S4), the processing of the processor 301 proceeds to Step S5. In Step S5, the acquisition unit 3002 of the processor 301 acquires the product code included in the tag information from the tag information accepting unit 3001. Then, the registration unit 3008 of the processor 301 executes product registration on the basis of the acquired product code. After that, the processing of the processor 301 of the controller 300 returns to Step S1. That is, the registration unit 3008 determines that the acquisition unit 3002 has acquired the product code of the product housed in the basket 25 and executes the product registration. Meanwhile, in the case where it is determined that the tag information has not been accepted (No in Step S4), the processor 301 determines that no product is housed in the basket 25. Then, the processing of the processor 301 skips Step S5 and returns to Step S1. At this time, the display 31 may display that no product is housed in the basket 25.

Further, in the case where it is determined that the second information has not been input (No in Step S1), the processing of the processor 301 proceeds to Step S6. In Step S6, the setting unit 3007 of the processor 301 sets the radio wave intensity to be strong. Then, the output unit 3009 of the processor 301 outputs first information for setting the radio wave intensity to be strong to the wireless tag reader 4. Then, in Step S7, whether or not the designation-release information has been input to the input unit 3004 of the processor 301 is determined. That is, the input unit 3004 of the processor 301 determines whether or not the customer has touched a designation-release button of the touch panel 32 in order to release the designation of the product whose allergen information is displayed.

In the case where it is determined that the designation-release information has been input (Yes in Step S7), the processing of the processor 301 proceeds to Step S8. In Step S8, the tag information accepting unit 3001 of the processor 301 starts accepting the tag information. The acquisition unit 3002 of the processor 301 acquires the product code included in the accepted tag information and stores the acquired product code in the product code section 304 of the RAM 303. Then, in Step S9, the output unit 3009 of the processor 301 refers to the product master section 312 of the storage device 310 and reads the product name and the allergen information corresponding to the product code stored in the product code section 304. Then, the output unit 3009 of the processor 301 outputs the read product name and allergen information to the display 31. Then, the processing of the processor 301 returns to Step S1. That is, the tag information accepting unit 3001 of the processor 301 outputs all the accepted product codes to the display 31 in association with the product names and the allergen information included in the tag information. The display 31 displays the product name and the allergen information. In the case where the product names and the allergen information relating to the products specified by all the product codes accepted by the tag information accepting unit 3001 cannot be displayed on one screen, the display 31 is capable of scrolling the display screen automatically or by the customer's operation.

Further, the output unit 3009 of the processor 310 refers to the RAM 303 when outputting the product name and the allergen information in Step S9. In the case where there is a product that has been registered as a result of the reference, the output unit 3009 of the processor 310 excludes the product that has been registered from the output target. It is presumed that the allergen information of the product that has been registered is checked before the product registration. For this reason, if allergen information or the like is displayed again for the product that has been registered, there is a possibility that the customer is confused. In order to avoid this, the product that has been registered is excluded from the output target.

Further, in the case where it is determined in the above-mentioned Step S7 that the designation-release information has not been input (No in Step S7), the processing of the processor 301 proceeds to Step S10. In Step S10, the processor 301 determines whether or not the designation information has been input to the input unit 3004 from the extraction unit 3003 or the touch panel 32. In the case where it is determined that the designation information has been input (Yes in Step S10), the processing of the processor 301 proceeds to Step S11. In Step S11, the designation unit 3005 of the processor 301 designates a product. The tag information accepting unit 3001 of the processor 301 starts accepting the tag information. The acquisition unit 3002 of the processor 301 acquires the product code included in the tag information from the tag information accepting unit 3001 and stores the acquired product code in the product code section 304 of the RAM 303.

Subsequently, in Step S12, the output unit 3009 of the processor 301 refers to the product master section 312 of the storage device 310 for the designated product, and reads the product name and the allergen information corresponding to the product code stored in the product code section 304. Then, the output unit 3009 of the processor 301 outputs the read trade name and allergen information to the display 31. Then, the processing of the processor 301 returns to Step S1. That is, the product name and the allergen information included in the tag information are associated with each other and output to the display 31 for the product specified by the designation unit 3005, of the products specified by the product codes accepted by the tag information accepting unit 3001. The display 31 displays the product name and the allergen information in association with each other. Note that in the above-mentioned Step S10, in the case where it is determined that the designation information has not been input (No in Step S10), the processing of the processor 301 returns to the processing of Step S1.

Through the above-mentioned processing, the registration apparatus 3 is capable of registering the product housed in the basket 25 and displaying information relating to an allergen contained in the product displayed on the product display shelf. The allergen information can be displayed for all the products whose product codes have been read by the wireless tag reader 4, and may be displayed for only the product designated by the customer, of the products whose product codes have been read by the wireless tag reader 4.

Figure 10:
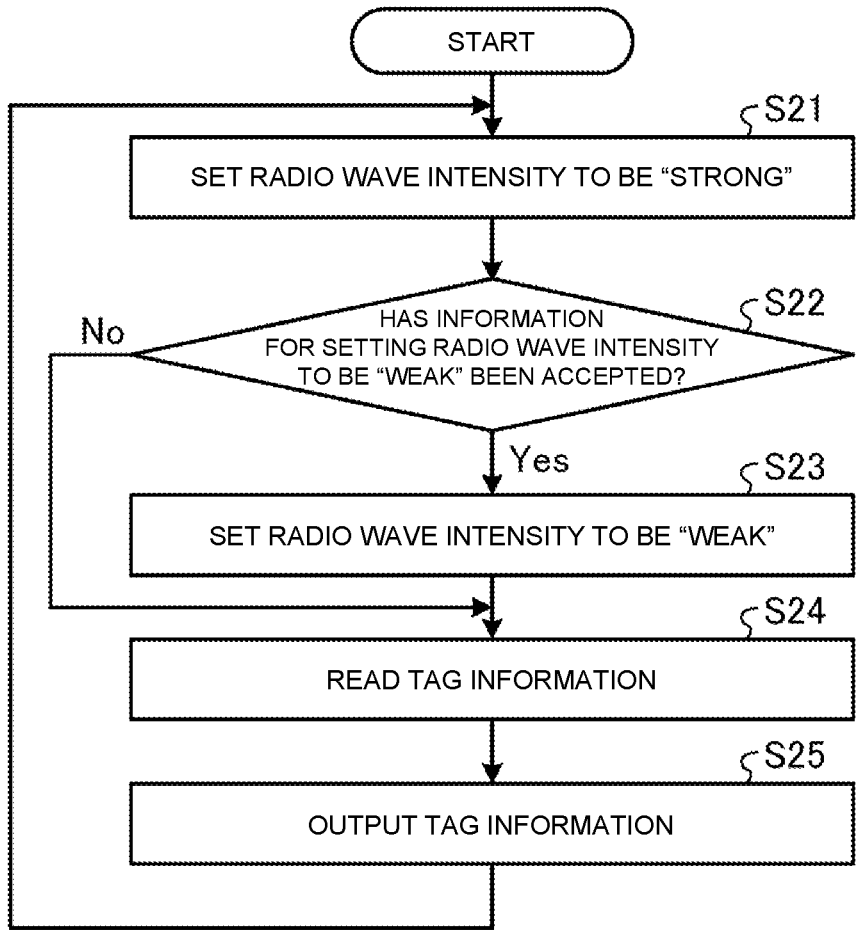
FIG. 10 is a flowchart showing processing of a controller of the wireless tag reader according to the embodiment.

Next, the processing executed by the wireless tag reader will be described. FIG. 10 is a flowchart showing the processing of the processor 401 of the controller 400 of the wireless tag reader 4.

First, in Step S21 shown in FIG. 10, when the operation of the wireless tag reader 4 starts, the radio wave intensity setting unit 4002 of the processor 401 sets the radio wave transmitted from the antenna 41 to the first radio wave intensity. Subsequently, in Step S22, the setting information accepting unit 4001 of the processor 401 determines whether or not second information indicating that the radio wave intensity is set to be weak has been accepted.

In the case where it is determined that the second information has been accepted (Yes in Step S22), the processing of the processor 401 proceeds to Step S23. In Step S23, the radio wave intensity setting unit 4002 of the processor 401 sets the radio wave intensity to the second radio wave intensity weaker than the first radio wave intensity. Subsequently, in Step S24, the reading unit 4003 of the processor 401 reads the tag information from response wave received by the antenna 41. Meanwhile, in Step S22, in the case where it is determined that the second information has not been accepted (No in Step S22), the processing of the processor 401 skips Step S23 and proceeds to Step S24. Subsequently, in Step S25, the tag information output unit 4004 of the processor 401 outputs the read tag information to the registration apparatus 3. Then, the processing of the processor 401 returns to Step S21.

By the above-mentioned processing, the wireless tag reader 4 is capable of reading the tag information from the wireless tag 43 attached to the product placed on the product display shelf and reading the tag information from the wireless tag 43 attached to the product housed in the basket 25.

As described above, in the registration apparatus 3 according to this embodiment, the acquisition unit 3002 of the processor 301 acquires the allergen information indicating the allergen contained in the product on the basis of the tag information of the wireless tag 43 attached to the product. For this reason, the registration apparatus 3 is capable of acquiring and displaying the allergen information of the actually existing product. For example, in the case where the allergen information of the product displayed on the product display shelf is stored in the wireless tag 43 provided on the product display shelf as in the existing technology, the registration apparatus according to the existing technology displays the allergen information even for the product that is not present on the product display shelf due to sold out or the like. Meanwhile, the registration apparatus 3 according to this embodiment does not display the allergen information of the product that is not present on the product display shelf, and does not confuse the customer.

Further, the processor 301 of the registration apparatus 3 according to this embodiment includes the acquisition unit 3002 that acquires allergen information for a designated product, and the output unit 3009 that outputs the allergen information acquired by the acquisition unit 3002. For this reason, the registration apparatus 3 according to this embodiment is capable of limiting the display of the allergen information for the product that seems to be unnecessary for the customer. Therefore, the registration apparatus 3 according to this embodiment is capable of easily grasping the allergen information necessary for the customer.

Further, the registration apparatus 3 according to this embodiment is capable of designating a product whose allergen information is displayed by the operation of the customer. In this case, by inputting the shelf number and the product type to the touch panel 32, a plurality of products can be designated by one operation, and operability can be improved.

Further, the registration apparatus 3 according to this embodiment is capable of specifying a product in accordance with the number of products specified by the product code included in the tag information read by the wireless tag reader 4. For this reason, the registration apparatus 3 according to this embodiment is capable of specifying the product that seems to be necessary for the customer and displaying the allergen information of the product. Therefore, the registration apparatus 3 according to this embodiment is capable of designating a product without performing an operation by the customer himself/herself, and the operability can be further improved.

In addition, the processor 301 of the registration apparatus 3 according to this embodiment includes the designation-release unit 3006 capable of releasing the designation of the product. For this reason, the registration apparatus 3 according to this embodiment is capable of also displaying all pieces of allergen information read by the wireless tag reader 4 as necessary. Therefore, the registration apparatus 3 according to this embodiment is capable of improving the convenience of the customer.

Further, the processor 301 of the registration apparatus 3 according to this embodiment includes the setting unit 3007. The setting unit 3007 is capable of setting the reading range of the wireless tag reader 4 to the first reading range in which the tag information is read from the wireless tag 43 attached to the product displayed in the product display shelf of the store, and to the second reading range in which the tag information of the wireless tag 43 attached to the product housed in the basket 25 is read, which is narrower than the first reading range. For this reason, the registration apparatus 3 according to this embodiment is capable of using the wireless tag reader 4 included in the cart 1 not only for displaying allergen information but also for product registration. Therefore, the registration apparatus 3 according to this embodiment is capable of displaying the allergen information without complicating the structure.

Note that in the above-mentioned embodiment, the control program executed by the registration apparatus 3 and the wireless tag reader 4 may be recorded on a computer-readable recording medium such as a CD-ROM and provided. Further, the control program executed by the registration apparatus 3 and the wireless tag reader 4 according to the above-mentioned embodiment may be stored in a computer connected to a network such as the Internet and downloaded via a network, or may be provided via a network such as the Internet.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An information processing apparatus mounted on a shopping cart used in a store, comprising:
    a wireless tag reader configured to read, from a wireless tag attached to a product within a particular range from the shopping cart in the store, tag information stored in the wireless tag, the tag information including identification data of the product;
    a storage device that stores a product master file for storing, in association with the identification data, a product name of the product and allergen information indicating an allergen contained in the product;
    a display; and
    a processor configured to:
        when one or more pieces of tag information are read by the wireless tag reader from one or more wireless tags within the particular range in the store, acquire, from the product master file, a product name and allergen information associated with each of one or more pieces of identification data included in said one or more pieces of tag information,
        accept an input of designation information for designating one of products specified by said one or more pieces of identification data, and
        control the display to display the product name and the allergen information of said one of products on a basis of the accepted designation information.

2. The information processing apparatus according to claim 1, further comprising
    an input device by which the designation information can be input by an operation of a user.

3. The information processing apparatus according to claim 2, wherein
    the designation information input by the input device includes the identification data for specifying said one of the products product, and
    the processor
        controls the display to display the product name and the allergen information of said one of products using the identification data included in the designation information.

4. The information processing apparatus according to claim 2, wherein
    the designation information input by the input device includes a product type indicating a type of said one of products,
    the storage device further stores a designation information file for storing the product type and the identification data in association with each other, and
    the processor is further configured to
        refer to the designation information file to specify said one of products having the identification data corresponding to the product type included in the designation information.

5. The information processing apparatus according to claim 1, wherein
    the storage device further stores a designation information file for storing product types each indicating a type of a product in association with identification data thereof, and
    the processor is further configured to:
        when a plurality of pieces of tag information are read by the wireless tag reader from a plurality of wireless tags, select a product type corresponding to the largest number of pieces of identification data included in the plurality of pieces of tag information,
        refer to the designation information file to specify one or more pieces of identification data associated with the selected product type, and
        control the display to display the product name and the allergen information associated with each of said one or more pieces of identification data.

6. The information processing apparatus according to claim 1, wherein
    tag information stored in a wireless tag further includes a product type, and
    the processor is further configured to:
        when a plurality of pieces of tag information are read by the wireless tag reader from a plurality of wireless tags, calculate the number of pieces of identification data included in the plurality of pieces of tag information for each product type,
        specify, in accordance with the calculated number of pieces of identification data for each product type, one of the pieces of identification data, and
        control the display to display the product name and the allergen information associated with said one of the pieces of identification data.

7. The information processing apparatus according to claim 1, further comprising an input device by which the input of designation information can be cancelled, wherein the processor is further configured to, when the input is cancelled by the input device, control the display to display the product name and the allergen information associated with each of said one or more pieces of identification data included in all of said one or more pieces of tag information read by the wireless tag reader.

8. The information processing apparatus according to claim 7, further comprising a memory that stores said one or more pieces of identification data included in said one or more pieces of tag information read by the wireless tag reader, wherein the processor acquires, from the product master file, the product name and the allergen information of each of the products having said one or more pieces of identification data stored in the memory.

9. The information processing apparatus according to claim 1, wherein the processor is further configured to:

set a reading range of the wireless tag reader to a first reading range in which tag information is read from a wireless tag attached to a product displayed on a product display shelf in the store, and to a second reading range in which tag information is read from a wireless tag attached to a product placed in the shopping cart, the second reading range being narrower than the first reading range, and register sales of a product purchased by a customer on a basis of identification data included in tag information read by the wireless tag reader while the reading range of the wireless tag reader is set to the second reading range.

10. An information processing method performed by an information processing apparatus mounted on a shopping cart used in a store, the information processing apparatus having a storage device that stores a product master file for storing, in association with identification data for specifying a product, a product name of the product and allergen information indicating an allergen contained in the product, the method comprising:

reading, by a wireless tag reader from one or more wireless tags attached to one or more products within a particular range from the shopping cart in the store, one or more pieces of tag information stored in the wireless tags;

acquiring, from the product master file, a product name and allergen information associated with each of one or more pieces of identification data included in said one or more pieces of tag information;

accepting an input of designation information for designating one of products specified by said one or more pieces of identification data; and displaying the product name and the allergen information of said one of products on a basis of the accepted designation information.

* * * * *

UNITED STATES PATENT AND TRADEMARK OFFICE
CERTIFICATE OF CORRECTION

PATENT NO. : 11,568,158 B2
APPLICATION NO. : 17/323998
DATED : January 31, 2023
INVENTOR(S) : Akiko Inoue Page 1 of 1

It is certified that error appears in the above-identified patent and that said Letters Patent is hereby corrected as shown below:

On the Title Page

(57) ABSTRACT, Line 10, replace "he" with --the--.

In the Claims

Column 14, Line 13, delete "product".

Signed and Sealed this
Twenty-first Day of November, 2023

Katherine Kelly Vidal
*Director of the United States Patent and Trademark Office*